United States Patent
Sasaki et al.

(10) Patent No.: US 7,135,014 B2
(45) Date of Patent: Nov. 14, 2006

(54) DIAPER WITH THIGH ELASTICS POSITIONED BENEATH INNER PAD AND OVERLAPPING SECOND ELASTICS POSITIONED ABOVE BACKSHEET

(75) Inventors: Toru Sasaki, Kagawa-ken (JP); Yoshikazu Tanaka, Kagawa-ken (JP); Hirotomo Mukai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 406 days.

(21) Appl. No.: 10/277,416

(22) Filed: Oct. 22, 2002

(65) Prior Publication Data

US 2003/0078556 A1 Apr. 24, 2003

(30) Foreign Application Priority Data

Oct. 24, 2001 (JP) .............................. 2001-326430

(51) Int. Cl.
*A61F 13/494* (2006.01)
(52) U.S. Cl. ....................... 604/385.28; 604/385.26; 604/385.01
(58) Field of Classification Search ............................. 604/385.24–385.27, 385.101, 385.01, 385.29, 604/358
See application file for complete search history.

(56) References Cited

U.S. PATENT DOCUMENTS

| | | | | |
|---|---|---|---|---|
| 4,743,246 A | * | 5/1988 | Lawson | 604/385.27 |
| 4,846,825 A | | 7/1989 | McMorrow et al. | |
| 4,904,251 A | * | 2/1990 | Igaue et al. | 604/385.26 |
| 5,163,932 A | * | 11/1992 | Nomura et al. | 604/385.29 |
| 5,447,508 A | * | 9/1995 | Numano et al. | 604/385.27 |
| 5,599,417 A | * | 2/1997 | Glaug et al. | 156/227 |
| 5,634,917 A | * | 6/1997 | Fujioka et al. | 604/385.29 |
| 5,749,865 A | * | 5/1998 | Yamamoto et al. | 604/385.29 |
| 5,906,603 A | * | 5/1999 | Roe et al. | 604/385.24 |
| 5,993,433 A | * | 11/1999 | St. Louis et al. | 604/385.27 |
| 6,306,122 B1 | * | 10/2001 | Narawa et al. | 604/385.3 |
| 6,423,042 B1 | * | 7/2002 | Sasaki | 604/385.01 |
| 6,638,262 B1 | * | 10/2003 | Suzuki et al. | 604/385.28 |
| 2001/0007936 A1 | * | 7/2001 | Shimoe et al. | 604/385.24 |
| 2002/0049421 A1 | * | 4/2002 | Hayase et al. | 604/385.27 |
| 2005/0038404 A1 | * | 2/2005 | Takino et al. | 604/385.27 |

FOREIGN PATENT DOCUMENTS

| | | |
|---|---|---|
| EP | 0 692 233 | 9/1998 |
| EP | 692233 B1 * | 9/1998 |
| EP | 0 901 780 | 3/1999 |
| JP | 1997-75390 A | 3/1997 |
| WO | WO 02/49560 | 6/2002 |
| WO | WO 03/063748 | 8/2003 |

\* cited by examiner

*Primary Examiner*—Tatyana Zalukaeva
*Assistant Examiner*—Laura C. Hill
(74) *Attorney, Agent, or Firm*—Butzel Long (57) ABSTRACT

A disposable diaper that includes an outer sheet having thigh-surrounding peripheral side regions curving inwardly in a transverse direction and an inner pad disposed to the inner side of the outer sheet. The outer sheet is provide in thigh-surrounding peripheral side regions with first elastic members. The inner pad is provided in its side flaps with second elastic members. The first and second members cross one another in front and rear regions of the thigh-surrounding peripheral side regions and free regions of the side flaps are bonded at the cross regions of the first and second elastic members to the thigh-surrounding side regions, so that the first and second members are substantially connected to one another.

7 Claims, 8 Drawing Sheets

DIAPER WITH THIGH ELASTICS POSITIONED BENEATH INNER PAD AND OVERLAPPING SECOND ELASTICS POSITIONED ABOVE BACKSHEET

BACKGROUND OF THE INVENTION

This invention relates to a disposable diaper for absorption and containment of bodily discharges.

Japanese Patent Publication No. 1997-75390A discloses a pants-type disposable diaper having a waist-hole and a pair of leg-holes, comprising an outer sheet having front and rear waist regions opposed to each other and a crotch region extending between these waist regions and an inner pad disposed to the inner side of the outer sheet so as to extend over a full length of the crotch region and further into the front and rear waist regions.

The outer sheet has waist-surrounding peripheral side regions extending across the front and rear waist regions, respectively, in a transverse direction, respective transversely opposite side regions of the front and rear waist regions extending in a longitudinal direction and transversely opposite thigh-surrounding peripheral side regions of the crotch region extending over full length of the crotch region in the longitudinal direction. These thigh-surrounding peripheral side regions curve inwardly in the transverse direction of the outer sheet. The front and rear waist regions are overlaid along the respective side regions thereof and joined together in the vicinity of outermost edges of these side regions by means of a plurality of heat-sealing lines arranged intermittently in the longitudinal direction along these side regions thereof. The front and rear waist regions are provided with suspenders extending downward from the respective waist-surrounding peripheral side regions toward the crotch region and a plurality of elastic members extending in the transverse direction, secured thereto in a stretched state.

The inner pad comprises a liquid-pervious topsheet facing a wearer's skin, a liquid-impervious backsheet facing away from a wearer's skin and a liquid-absorbent core interposed between these top- and backsheets. The inner pad has a rectangular shape being relatively long in the longitudinal direction and has a pair of side flaps generally rectilinearly extending along transverse opposite side edges of the core in the longitudinal direction. The side flaps are further provided respectively with stretchable elastic members generally rectilinearly extending in the longitudinal direction and secured thereto in a stretched state. The inner pad has its longitudinally opposite ends adapted to be detachably attached to the respective suspenders provided on the outer sheet.

In the case of the diaper disclosed in the above-cited Publication, both the side flaps of the inner pad and the elastic members secured thereto generally rectilinearly extend in the longitudinal direction of the diaper. With such an arrangement, both the side flaps and the elastic members never extend around wearer s thighs in a circumferential direction thereof when the diaper is worn. It is impossible therefore to put the side flaps of the inner pad closely around wearer's thighs utilizing a contractile force of the elastic members and it is likely that undesirable gaps might be formed between the side flaps and a wearer's skin and excretion discharged on the inner pad might leak out beyond the side flaps.

SUMMARY OF THE INVENTION

It is an object of this invention to provide a disposable diaper improved so that the side flaps of the inner pad can be put closely around wearer's thighs and thereby leakage of bodily discharges beyond the side flaps can be reliably avoided.

According to this invention, there is provided a disposable diaper comprising an outer sheet composed of, in a longitudinal direction, a front waist region, a rear waist regions and a crotch region extending between the waist regions wherein a pair of thigh-surrounding peripheral side regions curve over a full length of the crotch region inwardly in a transverse direction, an inner pad disposed to the inner side of the outer sheet and extending between the front and rear waist regions, the inner pad comprising a liquid-absorbent core and a liquid-pervious topsheet covering at least a top surface of the core, a pair of side flaps extending in the longitudinal direction along transversely opposite side edges of the core, stretchable first elastic members contractible secured to the respective thigh-surrounding peripheral side regions, curving inwardly of the outer sheet and stretchable second elastic members contractibly secured to the side flaps, extending rectilinearly in the longitudinal direction.

The diaper further comprises the thigh-surrounding peripheral side regions of the outer sheet respectively having front regions extending on a side of the front waist region, rear regions extending on a side of the rear waist region and intermediate regions respectively extending between the front and rear regions, the first elastic members being secured to the front and rear regions and intermediate regions, at least to the front and rear regions so that the first elastic members cross the second elastic members in the front and rear regions of the thigh-surrounding peripheral side regions; and the side flaps respectively having free inner side regions lying in a vicinity of the side edges of the core, free outer side regions lying outside the free inner side regions and fixed end regions lying on the front and rear waist regions of the outer sheet wherein the free inner side regions and the free outer side regions, at least the free inner side regions of the side flaps are joined to the thigh-surrounding peripheral side regions of the outer sheet at least in one of two cross regions of the first elastic members and the second elastic members.

This invention includes the following preferred embodiments.

The first elastic members and the second elastic members cross each other in a vicinity of transient regions between the front regions and the intermediate regions of the thigh-surrounding peripheral side regions and in the vicinity of transient regions between the rear regions and the intermediate regions of the thigh-surrounding peripheral side regions.

The side flaps are respectively provided with a plurality of the second elastic members arranged so as to be spaced one from another in the transverse direction between the free inner side regions and the free outer side regions by a given dimension.

The fixed end regions of the side flaps are folded inward in the transverse direction of the pad and bonded to the pad in such a folded state.

The outer sheet is made of hydrophobic fibrous nonwoven fabrics.

Transversely opposite waist side regions extending over a full length of the front waist region in the longitudinal direction are connected to the associated waist side regions extending over a full length of the rear waist region so as to define a waist-hole and a pair of leg-holes.

DETAILED DESCRIPTION OF THE PREFERRED EMBODIMENTS

Details of the disposable diaper according to this invention will be more fully understood from the description given hereunder in reference to the accompanying drawings.

Figure 1:
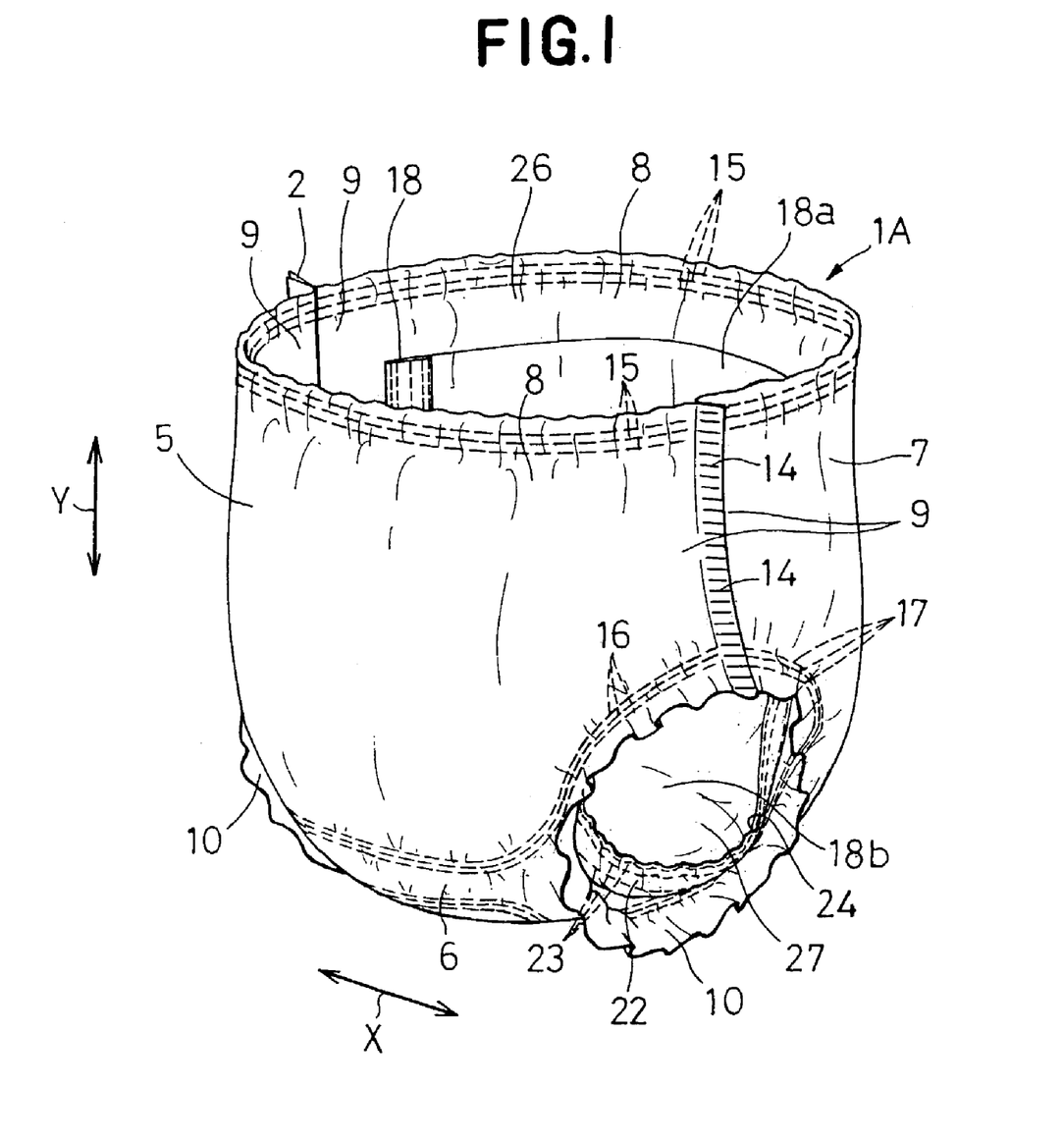
FIG. 1 is a perspective view of one embodiment of the diaper according to this invention.
Figure 2:
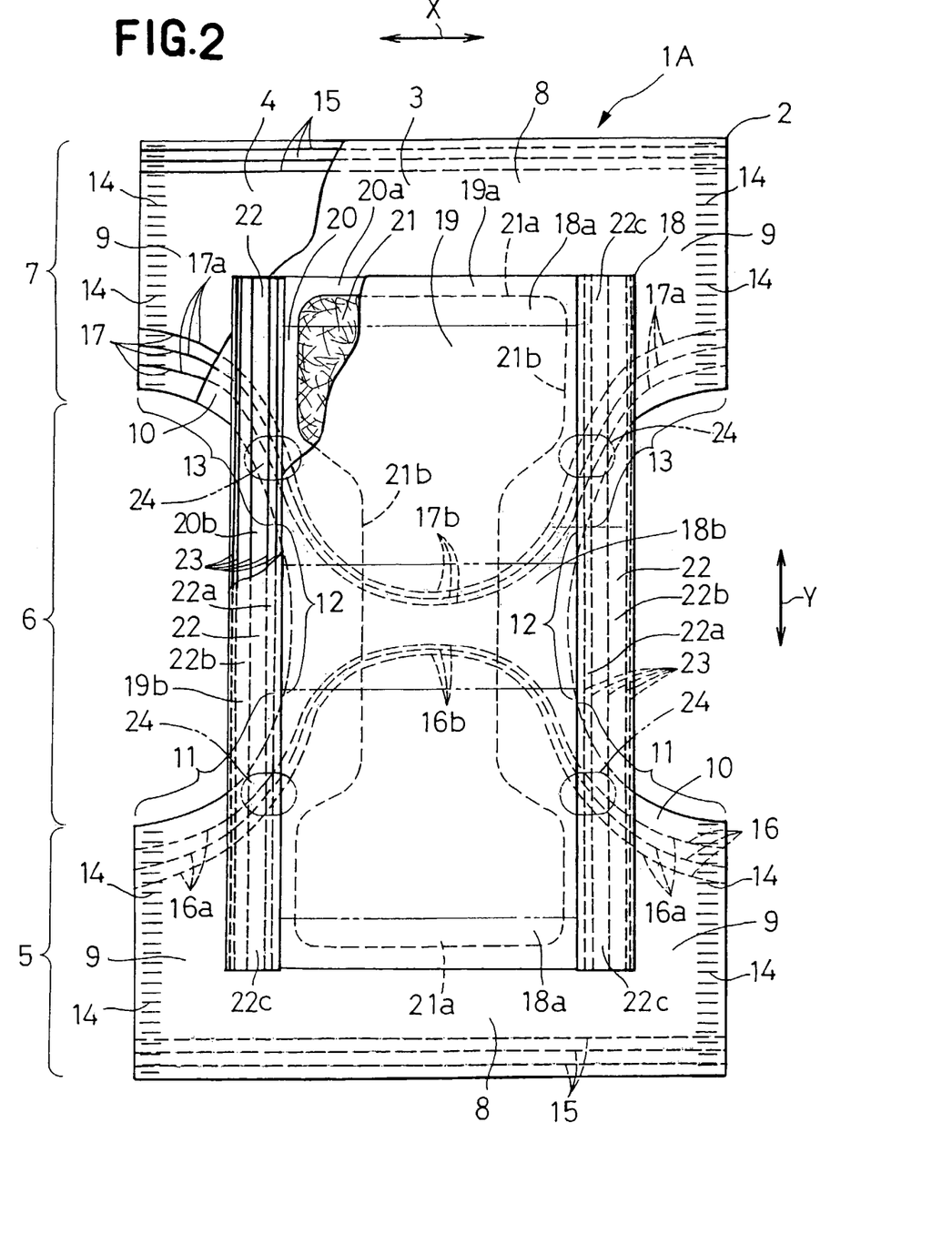
FIG. 2 is a partially cutaway plan view of this diaper as the front and rear waist regions having been disconnected from each other.
Figure 3:
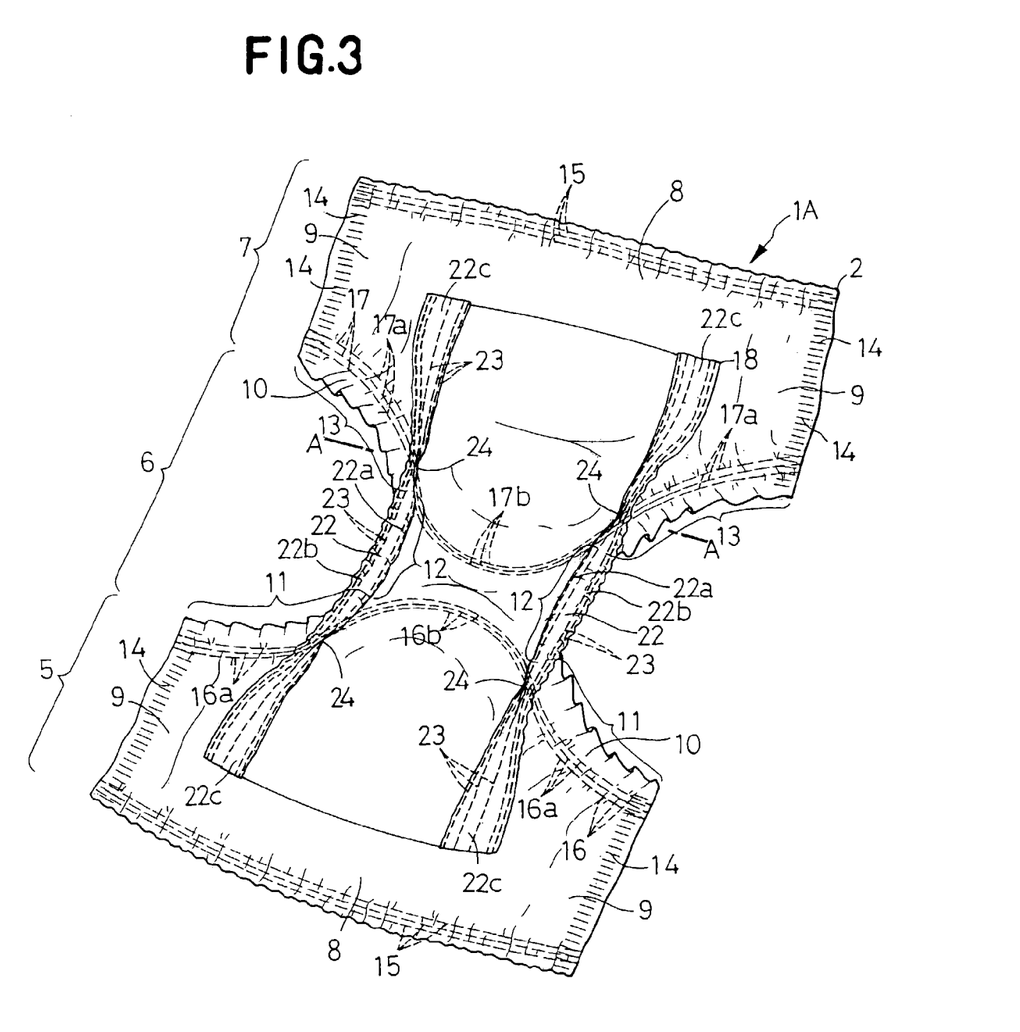
FIG. 3 is a perspective view showing this diaper as the front and rear waist regions having been disconnected from each other.
Figure 4:
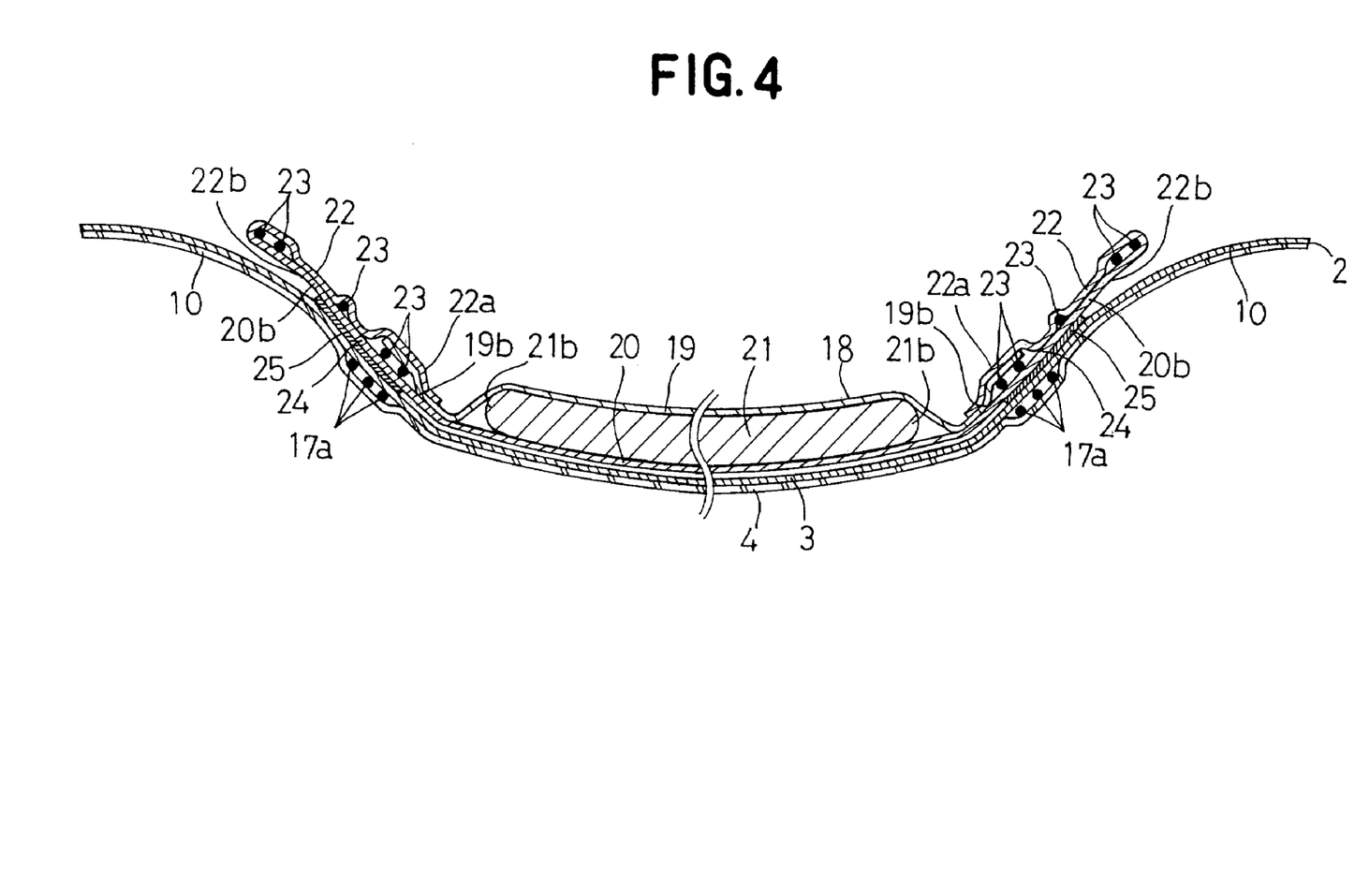
FIG. 4 is a sectional view taken along a line A—A in FIG. 3.

FIGS. 1–4 show the first embodiment of the diaper according to this invention. FIG. 1 is a perspective view of the diaper 1A, FIG. 2 is a partially cutaway plan view showing the diaper as front and rear waist regions having been disconnected from each other, FIG. 3 is a perspective view showing the diaper as the front and rear waist regions having been disconnected from each other and FIG. 4 is a sectional view taken along a line A—A in FIG. 3. In FIGS. 1 and 2, a transverse direction is indicated by an arrow X and a longitudinal direction is indicated by an arrow Y. In FIG. 2, the diaper is shown in a stretched state in the longitudinal direction as well as in the transverse direction.

The diaper 1A comprising an outer sheet 2 and an inner pad 18 disposed to the inner side of the outer sheet 2 is of pants-type and has a waist-hole 26 and a pair of leg-holes 27.

The outer sheet 2 comprises inner and outer sheets 3, 4, which are formed by a hydrophobic fibrous nonwoven fabric overlaid and have surfaces thereof opposed and bonded to each other, and is composed of, in the longitudinal direction, a front waist region 5, a rear waist region 7 and a crotch region 6 extending between these waist regions 5, 7. The outer sheet 2 defines waist-surrounding peripheral side regions 8 extending across the front and rear waist regions 5, 7 in the transverse direction, transversely opposite waist side regions 9 extending over full length of the front and rear waist regions 5, 7 in the longitudinal direction and thigh-surrounding peripheral side regions 10 curving inwardly in the transverse direction. Accordingly, outer sheet 2 has an hourglass-like planar shape.

Each of the thigh-surrounding side regions 10 has a front region 11 extending on a side of the front waist region 5, a rear region 13 extending on a rear waist region 7 and an intermediate region 12 extending between the front and rear regions 11, 13. The regions 11, 12, 13 correspond to respective thirds defined by approximately trisecting the full length of the thigh-surrounding peripheral side region 10 of the outer sheet 2 in the longitudinal direction. The third extending on a side of the front waist region 5 defines the front region 11, the third extending on a side of the rear waist region 7 defines the rear region 13 and the third extending between the front and rear regions 11, 13 defines the intermediate region 12.

The front and rear waist regions 5, 7 are overlaid along the respective transversely opposite side regions 9 and joined together in the vicinity of the outermost edges thereof by means of a plurality of heat-sealing lines 14 intermittently arranged in the longitudinal direction.

The waist-surrounding peripheral side regions 8 are provided with a plurality of waist-surrounding elastic members 15 extending in the transverse direction and secured thereto in a stretched state. The crotch region 6 is provided in its approximately front half with a plurality of thigh-surrounding elastic members 16 (stretchable first elastic members) secured thereto in a stretched state. These elastic members 16 curve convexly from the side of the front waist region 5 toward the longitudinal middle of the crotch region 6. Similarly, the crotch region 6 is provided in its approximately rear half with a plurality of thigh-surrounding elastic members 17 (stretchable first elastic members) secured thereto in a stretched state. These elastic members 17 curve convexly from the side of the rear waist region 7 toward the longitudinal middle of the crotch region 6. The waist-surrounding elastic members 15 as well as the thigh-surrounding elastic members 16, 17 are interposed between the inner and outer sheets 3, 4 constituting the outer sheet 2 and secured to the inner and outer sheets 3, 4.

The thigh-surrounding elastic members 16, 17 respectively comprise transversely opposite lateral regions 16a, 17a extending along the front and rear regions 11, 13 of the respective thigh-surrounding peripheral side regions 10 and intermediate regions 16b, 17b extending across the crotch region 6. The lateral regions 16a, 17a of these elastic members 16, 17 respectively curve along the front and rear regions 11, 13 of the respective thigh-surrounding peripheral side regions 10 inwardly in the transverse direction. The intermediate regions 16b, 17b of these elastic members 16, 17 are spaced from each other in the longitudinal direction by a given dimension in the crotch region 6.

The inner pad 18 has a rectangular planar shape being relatively long in the longitudinal direction and extends over the crotch region 6 and further into the front and rear waist regions 5, 7 of the outer sheet 2. The inner pad 18 comprises a liquid-pervious topsheet 19 facing a wearer's skin, a substantially liquid-impervious backsheet 20 facing away from a wearer's skin and a liquid-absorbent core 21 interposed between the top- and backsheets 19, 20. The core 21 is bonded to the inner surface of at least one of the top- and backsheets 19, 20. The inner pad 18 has a pair of side flaps 22 generally rectilinearly extending in the longitudinal direction along transversely opposite side edges 21b of the core 21.

The inner pad 18 has its longitudinally opposite end regions 18a bonded to about the middle in the longitudinal direction of the front and rear waist regions 5, 7 and its middle region 18b bonded to the crotch region 6 of the outer sheet 2. The inner pad 18 has regions defined between the end regions 18a and the intermediate region 18b not bonded to the outer sheet 2 and therefore being free with respect to the outer sheet 2. In the end regions 18a and the intermediate region 18b, the outer surfaces of the backsheet 20 constituting the inner pad 18 are bonded to the inner sheet 3 constituting the outer sheet 2.

Each of the side flaps 22 extends in the longitudinal direction immediately outside the associated inside edge 21b of the core 21 and has a free inner side region 22a, a free outer side region 22b outside the free inner side region 22a and fixed longitudinally opposite end regions 22c fixed to the front and rear waist regions 5, 7 of the outer sheet 2. The free inner side region 22a and the free outer side region 22b of the side flaps 22 are provided with a plurality of stretchable elastic members 23 (stretchable second elastic members) generally rectilinearly extending in the longitudinal direction and attached in a stretched state and are spaced one from another in the transverse direction.

The thigh-surrounding elastic members 16, 17 of the outer sheet 2 cross the elastic members 23 of the respective side flaps 22 in the front side regions 11 and the rear side regions 13 of the respective thigh-surrounding peripheral side regions 10. More specifically, the thigh-surrounding elastic members 16, 17 cross the elastic members 23 in the vicinity of transient points between the respective front regions 11 and the respective intermediate regions 12 of the thigh-surrounding peripheral side regions 10 as well as in the vicinity of transient points between the respective rear regions 13 and the respective intermediate regions 12 of the thigh-surrounding peripheral side regions 10. The free inner side regions 22a of the respective side flaps 22 are bonded to the thigh-surrounding peripheral side regions 10 of the outer sheet 2 at cross regions 24 of the thigh-surrounding elastic members 16, 17 and the elastic members 23. At these cross regions 24, the under surface of the backsheet 20 constituting the inner pad 18 is bonded to the inner sheet 3 of the outer sheet 2 by means of a hot melt adhesive 25.

As described above, the free inner side regions 22a of the respective side flaps 22 are bonded to the respective thigh-surrounding peripheral side regions 10 of the outer sheet 2 at the cross regions 24. Consequently, the thigh-surrounding peripheral side regions 10 are substantially connected to the side flaps 21 and the thigh-surrounding elastic members 16, 17 are substantially connected to the elastic members 23.

The thigh-surrounding peripheral side regions 10 and the side flaps 22 being contiguous to the respective thigh-surrounding peripheral side regions 10 extend in a circumferential direction around wearer's thighs as the diaper 1A is worn. At the same time, the lateral regions 16a, 17a of the respective thigh-surrounding elastic members 16, 17 are stretched in the circumferential direction around the wearer's thighs and thereby stretch the elastic members 23 in the circumferential direction around the wearer's thighs. Between each pair of the adjacent cross regions 24 of these elastic members 16, 17, 23, a contractile force of the elastic members 23 causes the free inner and outer side regions 22a, 22b of the respective side flaps 22 to be tightly placed around the wearer's thighs. Along the front regions 11 and the rear regions 13 of the respective thigh-surrounding peripheral side regions 10, a contractile force of the lateral regions 16a, 17a of the respective thigh-surrounding elastic members 16, 17 causes the thigh-surrounding peripheral side regions 10 of the outer sheet 2 to be tightly placed around the wearer's thighs.

The inner pad 18 curves in the longitudinal direction with the topsheet 19 inside as will be seen in FIG. 1 and contraction of the elastic members 23 causes the free inner and outer side regions 22a, 22b of the side flaps 22 extending between each pair of the adjacent cross regions 24 to rise on the topsheet 19. The side flaps 22 of the inner pad 18 extending between each pair of the adjacent cross regions 24 are tightly placed around wearer's thighs and thereby form barriers against bodily discharges. In this way, no gap is left between the wearer's thighs and the side flaps 22 and it is not likely that any amount of bodily discharges might leak beyond the side flaps 22. The free outer side regions 22b of the respective side flaps 22 are not bonded to the thigh-surrounding peripheral side regions 10 of the outer sheet 2 at the cross regions 24, so these free outer side regions 22b can rise on the topsheet 19 at these cross regions 24 and thereby prevent any amount of bodily discharges from leaking beyond these cross regions 24.

There is no anxiety that any amount of bodily discharges might leak beyond the thigh-surrounding peripheral side regions 10 even if any amount of bodily discharges leaks beyond the fixed end regions 22c of the side flaps 22. This is for the reason that, along the front regions 11 and the rear regions 13, the thigh-surrounding peripheral side regions 10 of the outer sheet 2 are tightly placed around wearer's thighs.

Along the longitudinally opposite end regions 18a of the inner pad 18, the top- and backsheets 19, 20 extend outward in the longitudinal direction beyond the longitudinally opposite ends 21a of the core 21 to define longitudinally opposite end regions 19a and longitudinally opposite end regions 20a of these sheets 19, 20 and the end regions 19a, 20a have inner surfaces thereof bonded to each other.

The side flaps 22 of the inner pad 18 comprise transversely opposite side regions 19b of the topsheet 19 and transversely opposite side regions 20b of the backsheet 20 extending outward in the transverse direction beyond transversely opposite side edges 21b of the core 21. The side regions 20b of the backsheet 20 are folded back along the side edges of the free outer side regions 22b so as to be placed upon the respective side regions 19b of the topsheet 19 and the side regions 19b, 20b of the top- and backsheets 19, 20 placed upon each other in this manner are joined together. The elastic members 23 lying on the side of the free outer side regions 22b are interposed between two layers of the folded backsheet 20 and secured to the inner surfaces of the side regions 20b of the backsheet 20. The elastic members 23 lying on the side of the free inner side regions 22a are interposed between the top- and backsheets 19, 20 and secured to the inner surfaces of the side regions 19b, 20b of these sheets 19, 20.

Figure 5:
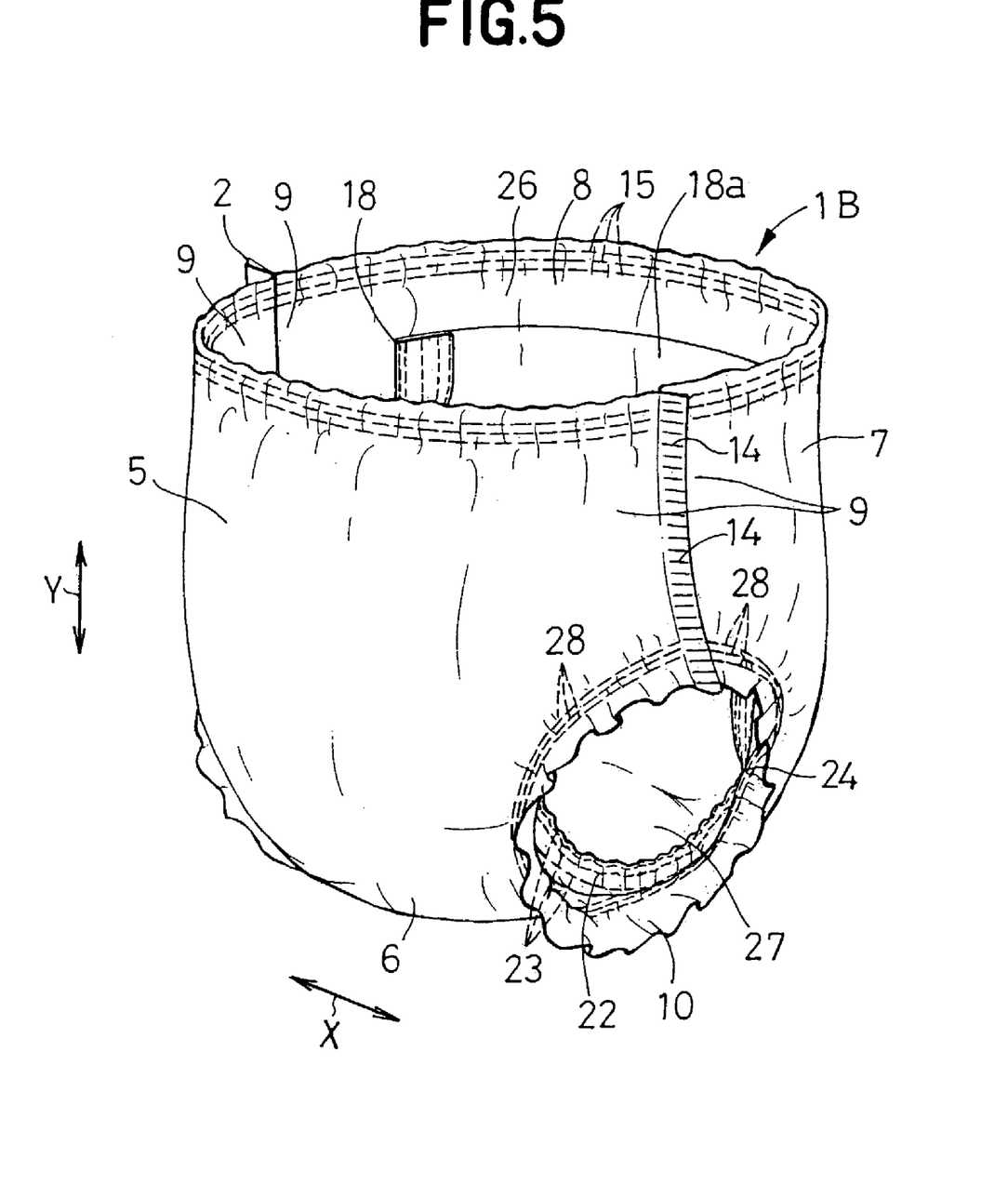
FIG. 5 is a perspective view of another embodiment of the diaper according to this invention.
Figure 6:
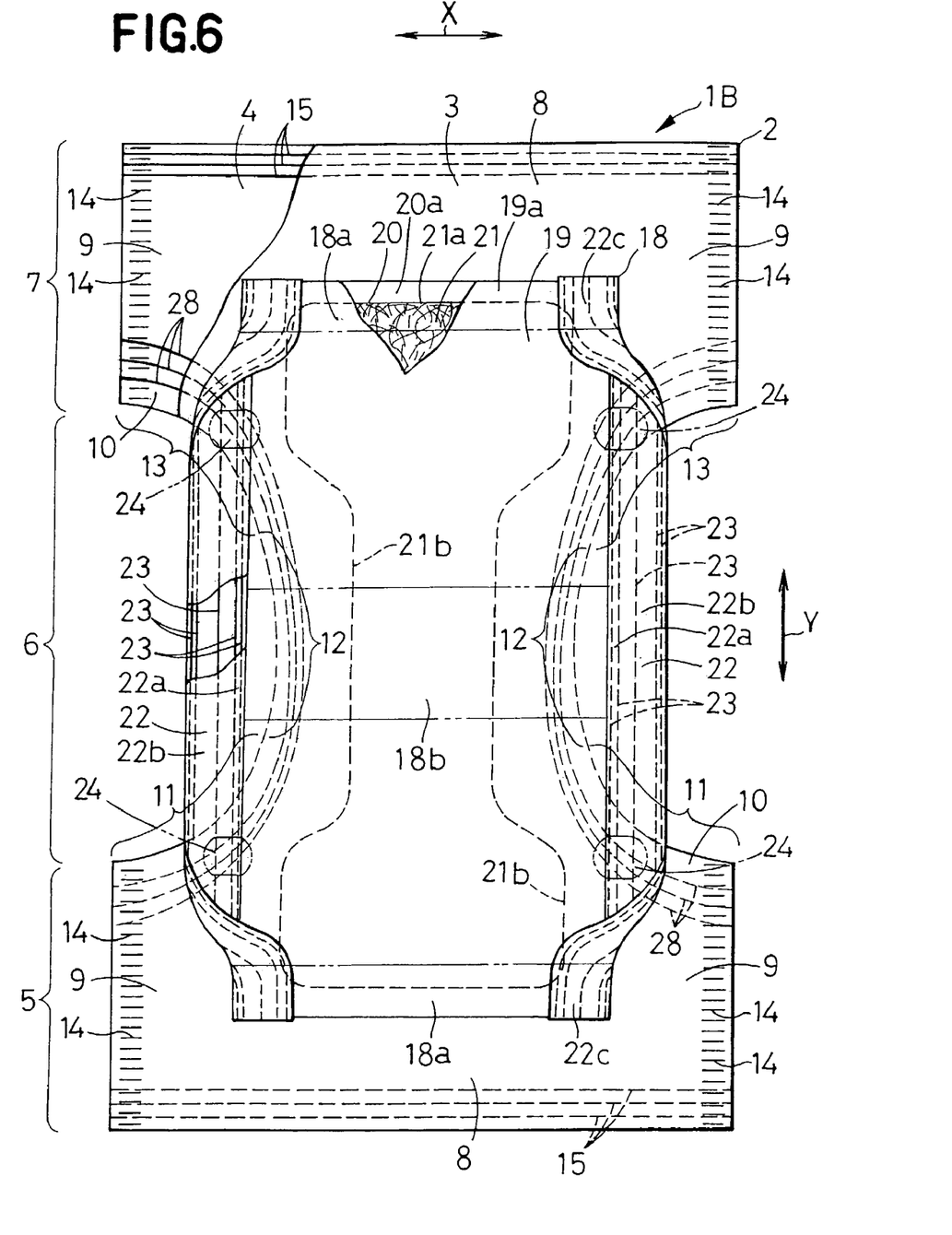
FIG. 6 is a partially cutaway plan view showing this diaper of FIG. 5 as the front and rear waist regions having been disconnected from each other.
Figure 7:
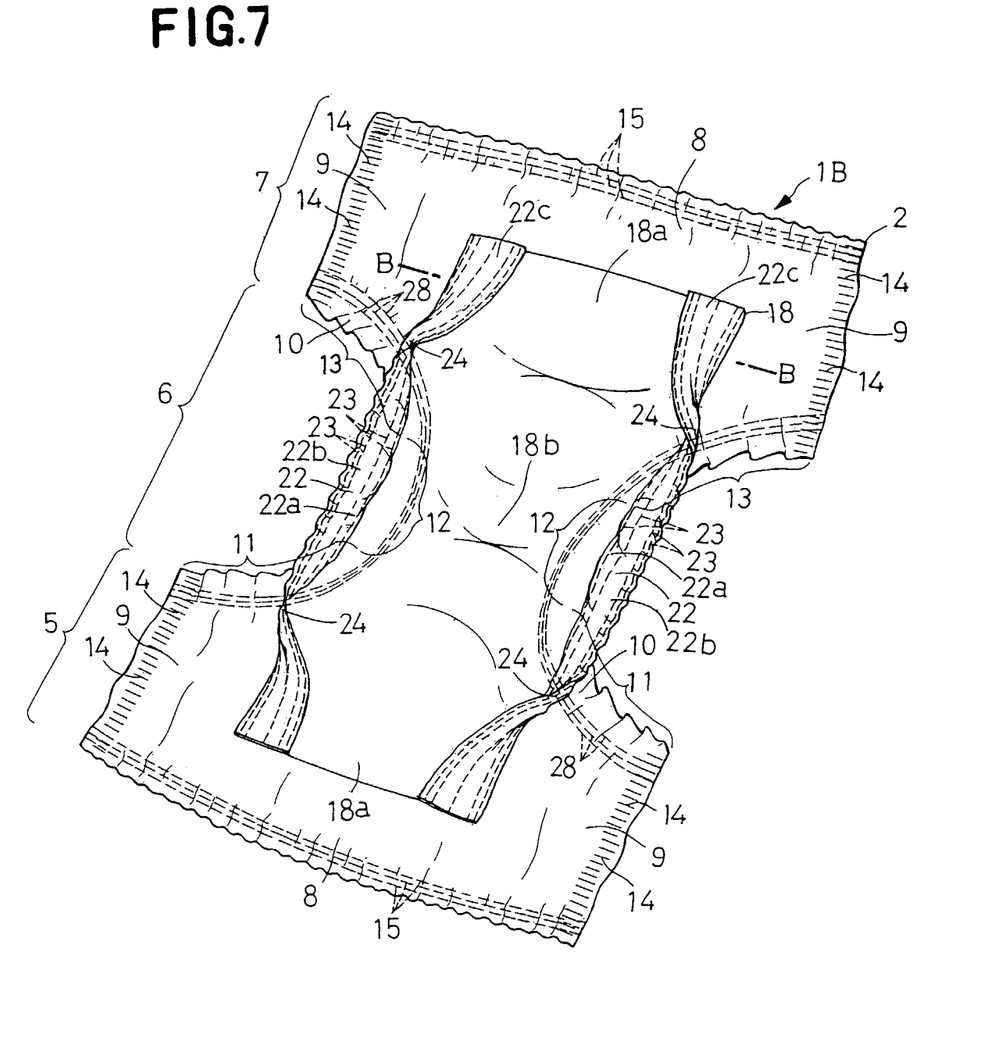
FIG. 7 is a partially cutaway perspective view showing this diaper of FIG. 5 as the front and rear waist regions having been disconnected from each other.
Figure 8:
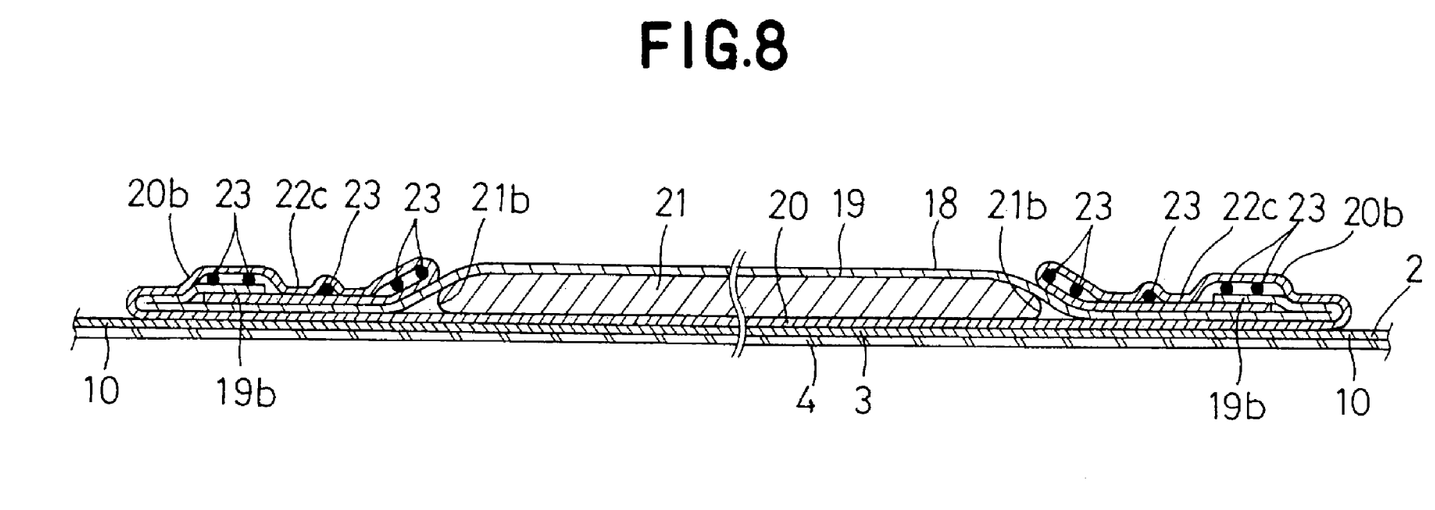
FIG. 8 is a sectional view taken along a line B—B in FIG. 7.

FIGS. 5–8 show the second embodiment of the diaper according to this invention. FIG. 5 is a perspective view of the diaper, FIG. 6 is a partially cutaway plan view showing this diaper of FIG. 5 as the front and rear waist regions having been disconnected from each other, FIG. 7 is a perspective view showing this diaper as the front and rear waist regions having been disconnected from each other and FIG. 8 is a sectional view taken along a line B—B in FIG. 7. In FIGS. 4 and 5, a transverse direction is indicated by an arrow X and a longitudinal direction is indicated by an arrow Y. In FIG. 5, the diaper is shown in a stretched state in the longitudinal direction as well as in the transverse direction.

Similarly to the diaper 1A shown in FIG. 1, the diaper 1B of this embodiment comprises an outer sheet 2 and an inner pad 18 attached to the inner side of the outer sheet 2. The diaper 1B is of pants-type and has a waist-hole 26 and a pair of leg-holes 27. The diaper 1B is distinguished from the diaper 1A shown in FIG. 1 in the arrangement as will be described.

The thigh-surrounding peripheral side regions 10 of the outer sheet 2 are provided with a plurality of thigh-surrounding elastic members 28 (stretchable first elastic members) secured thereto in a stretched state. The thigh-surrounding elastic members 28 extend along the front and rear regions 11, 13 and the intermediate regions 12 of the respective thigh-surrounding peripheral side regions 10 and curve along the thigh-surrounding peripheral side region 10 and curve along the thigh-surrounding peripheral side region 10 inwardly in the transverse direction of the outer sheet 2.

In the inner pad 18, the fixed end regions 22c of the respective side flaps 22 are folded inward in the transverse direction of the pad 18. These fixed end regions 22c are bonded to the upper surface of the topsheet 19.

The thigh-surrounding elastic members 28 of the outer sheet 2 cross the stretchable elastic members 23 (stretchable second elastic members) of the side flaps 22 at the front and rear regions 11, 13 of the respective thigh-surrounding peripheral side regions 10. The free inner side regions 22a and the free outer side regions 22b of the respective side flaps 22 are bonded to the thigh-surrounding peripheral side regions 10 of the outer sheet 2 at the cross regions 24 of the thigh-surrounding elastic members 28 and the elastic members 23. At these cross regions 24, the under surface of the backsheet 20 constituting the inner pad 18 is bonded to the inner sheet 3 of the outer sheet 2 by means of a hot melt adhesive (not shown).

The free inner side regions 22a and the free outer side regions 22b of the respective side flaps 22 are bonded to the respective thigh-surrounding peripheral side regions 10 of the outer sheet 2 at the cross regions 24. Consequently, the thigh-surrounding peripheral side regions 10 are substantially connected to the side flaps 22 and the thigh-surrounding elastic members 28 are substantially connected to the elastic members 23. The thigh-surrounding peripheral side regions 10 and the side flaps 22 being contiguous to the respective thigh-surrounding peripheral side regions 10 extend in a circumferential direction around wearer's thighs as the diaper 1B is worn. At the same time, the thigh-surrounding elastic members 28 and the elastic members 23 are stretched in the circumferential direction around the wearer's thighs.

Contraction of the elastic members 23, 28 causes the free inner and outer side regions 22a, 22b of the side flaps 22 extending between each pair of the adjacent cross regions 24 to be tightly placed around the wearer's thighs. Along the front regions 11 and the rear regions 13 of the respective thigh-surrounding peripheral side regions 10, a contractile force of the thigh-surrounding elastic members 28 causes these thigh-surrounding peripheral side regions 10 of the outer sheet 2 to be tightly placed around the wearer's thighs. The thigh-surrounding peripheral side regions 10 of the outer sheet 2 as well as the side flaps 22 of the inner pad 18 are tightly placed around the wearer's thighs in this manner, so there is no anxiety that any amount of bodily discharges might leak beyond the thigh-surrounding peripheral side regions 10 and the side flaps 22.

The fixed longitudinally opposite end regions 22c of the respective side flaps 22 are folded inward in the transverse direction of the inner pad 18, so the free inner and outer side regions 22a, 22b of the respective side flaps 22 extending in the vicinity of these fixed end regions 22c rise on the topsheet 19 as will be seen in FIG. 6. The side flaps 22 form barriers against bodily discharges not only between each pair of the adjacent cross regions 24 of the elastic members 23, 28 but also in the vicinity of the fixed end regions 22c, and thereby leakage of bodily discharges beyond the side flaps 22 can be reliably avoided between the cross regions 24 as well as in the vicinity of the fixed end regions 22c.

Stock material for the topsheet 19 may be selected from a group including a hydrophilic fibrous nonwoven fabric, a hydrophobic fibrous nonwoven fabric having a plurality of pores and a plastic film having a plurality of fine pores.

Stock material for the backsheet 20 may be selected from a group including a hydrophobic fibrous nonwoven fabric, a breathable but liquid-impervious plastic film, a composite nonwoven fabric comprising two or more hydrophobic fibrous nonwoven fabric layers laminated one upon another and a composite sheet comprising a hydrophobic fibrous nonwoven fabric and a breathable but liquid-impervious plastic film laminated with each other.

Stock material for the outer sheet 2 may be selected from a group including a hydrophobic fibrous nonwoven fabric, a breathable but liquid-impervious plastic film and a composite sheet comprising a hydrophobic fibrous nonwoven fabric and a breathable but liquid-impervious plastic film laminated with each other.

It is also possible to form the outer sheet 2 and the backsheet 20 using a composite nonwoven fabric comprising a melt blown fibrous nonwoven fabric having high a water-resistance sandwiched between spun bond fibrous nonwoven fabric layers each having a high strength and a desired flexibility.

The nonwoven fabric used for this invention may be selected from a group including products those made by spun lace-, needle punch-, melt blown-, thermal bond-, spun bond-, chemical bond- and air through-processes. Component fibers of the nonwoven fabric may be selected from a group consisting of polyolefine-; polyester- and polyamide-based fibers and core-sheath type or side-by-side type conjugated fibers of polyethylene/polypropylene or polyethylene/polyester.

The core 21 is a mixture of fluff pulp and super-absorbent polymer particles or a mixture of fluff pulp, super-absorbent polymer particles and thermoplastic synthetic resin fibers, in both cases, compressed to a desired thickness. Preferably, the core 21 is entirely covered with a liquid-pervious sheet such as a tissue paper or a hydrophilic fibrous nonwoven fabric to prevent the core 21 from getting out of shape and to prevent the polymer particles from falling off. As the polymer particles, a starch-based polymer, a cellulose-based polymer or a synthetic polymer may be used.

To bond the outer sheet 2 and the inner pad 18 to each other, to join the topsheet 19 and the backsheet 20 to bond the core 21 and to secure the elastic members 15, 16, 17, 23, 28, hot melt adhesives or thermally welding means such as a heat-sealing or an ultrasonic sealing may be used.

This invention is applicable not only to the pants-type disposable diaper in which the waist side edge regions of the front and rear waist regions have already been connected together but also to the open-type disposable diaper in which the waist side edge regions of the front and rear waist regions are connected together immediately before the diaper is worn.

The disposable diaper according to this invention has the advantageous effects that, of the free inner and outer side regions of the respective side flaps forming a part of the inner pad, at least the free inner side regions are bonded to the thigh-surrounding peripheral side regions of the outer sheet at the cross regions of the stretchable first elastic members and the stretchable second elastic members. With such a unique arrangement, the thigh-surrounding peripheral side regions are substantially connected to the side flaps and the first elastic members are substantially connected to the second elastic members. With the diaper put on a wearer's body, the second elastic members are stretched in a circumferential direction around wearer's thighs as the first elastic members are stretched in the circumferential direction around the wearer's thighs. In this diaper, a contractile force of the second elastic members causes the side flaps of the inner pad extending between each pair of the cross regions of these elastic members to be tightly placed around the wearer's thighs and thereby to form the barriers against bodily discharges. In this way, no gap is left between the wearer's thighs and the side flaps and leakage of bodily discharges beyond the side flaps can be reliably avoided.

In the case of the embodiment arranged so that the fixed longitudinally opposite end regions of the respective side flaps are folded inward in the transverse direction of the inner pad, the side flaps of the inner pad extending between each pair of the adjacent cross regions of the first and second elastic members form the barriers against bodily discharges. In this way, it is ensured to avoid leakage of bodily discharges beyond the side flaps which otherwise might occur not only between each pair of the adjacent cross regions of the elastic members but also in the vicinity of the fixed longitudinally opposite end regions.

What is claimed is:

1. A disposable diaper comprising:
    an outer sheet composed of:
        a front waist region;
        a rear waist region;
        a crotch region extending between the waist regions; and
        a pair of thigh-surrounding peripheral side regions that curve inwardly over a full length of said crotch region in a transverse direction;
    an inner pad disposed to the inner side of said outer sheet and extending between said front and rear waist regions, said inner pad comprising a liquid-pervious topsheet, a liquid-impervious backsheet and a liquid-absorbent core positioned between the liquid-pervious topsheet and the liquid-impervious backsheet of the inner pad;
    a pair of side flaps extending in said longitudinal direction along transversely opposite side edges of said core;
    stretchable first elastic members positioned beneath the inner pad and contractibly secured to the respective thigh-surrounding peripheral side regions, curving transversely inwardly; and
    stretchable second elastic members contractibly secured to said side flaps and being positioned above the liquid-impervious backsheet of the inner pad, and extending rectilinearly in said longitudinal direction, said thigh-surrounding peripheral side regions of said outer sheet respectively having:
        front regions extending on a side of said front waist region;
        rear regions extending on a side of said rear waist region; and
        intermediate regions respectively extending between said front and rear regions, said first elastic members being secured to at least to said front and rear regions so that said first elastic members cross said second elastic members in said front regions and rear regions of said thigh-surrounding peripheral side regions, said side flaps respectively having:
    proximal regions lying in a vicinity of side edges of said core, with at least one of said stretchable second elastic members extending alone said proximal regions;
    distal regions lying outside said proximal regions; and
    fixed end regions lying on said from and rear waist regions of said outer sheet, at least said proximal regions of said side flaps being joined to said thigh-surrounding peripheral side regions of said outer sheet at least in one of two cross regions of said first elastic members and said second elastic members.

2. The diaper according to claim 1, wherein said first elastic members and said second elastic members cross each other in a vicinity of transient regions between said front regions and said intermediate regions of said thigh-surrounding peripheral side regions and in a vicinity of transient regions between said rear regions and said intermediate regions of said thigh-surrounding peripheral side regions.

3. The diaper according to claim 1, wherein said-side flaps are respectively provided with a plurality of said second elastic members arranged so as to be spaced one from another in said transverse direction between said proximal regions and said distal regions by a given dimension.

4. The diaper according to claim 1, wherein said fixed end regions of said side flaps are folded inward in said transverse direction of said pad and bonded to said pad in such a folded state.

5. The diaper according to claim 1, wherein said outer sheet comprises hydrophobic fibrous nonwoven fabrics.

6. The diaper according to claim 1, wherein transversely opposite waist side regions extend over a full length of said front waist region in said longitudinal direction and are connected to said associated waist side regions extending over a full length of said rear waist region so as to define a waist-hole and a pair of leg-holes.

7. The diaper according to claim 1, wherein said proximal and distal regions of said side flaps between said two cross regions of said first and second elastic members are folded outward in said transverse direction of said pad in a longitudinal stretched state of said side flaps.

* * * * *

UNITED STATES PATENT AND TRADEMARK OFFICE
CERTIFICATE OF CORRECTION

PATENT NO. : 7,135,014 B2  Page 1 of 1
APPLICATION NO. : 10/277416
DATED : November 14, 2006
INVENTOR(S) : Toru Sasaki, Yoshikazu Tanaka and Hirotomo Mukai It is certified that error appears in the above-identified patent and that said Letters Patent is hereby corrected as shown below:

Column 1,
Line 60, should be changed from
"never extend around wearer s thighs in a circumferential;"
to
--never extend around wearer's thighs in a circumferential;--

Signed and Sealed this

Thirty-first Day of July, 2007

JON W. DUDAS
*Director of the United States Patent and Trademark Office*